United States Patent [19]

Logusch

[11] Patent Number: 4,764,620

[45] Date of Patent: Aug. 16, 1988

[54] 4-PHOSPHORUS-2-PHTHALIMIDOBUTY-RATE INTERMEDIATES

[75] Inventor: Eugene W. Logusch, St. Louis, Mo.

[73] Assignee: Monsanto Company, St. Louis, Mo.

[21] Appl. No.: 60,692

[22] Filed: Jun. 11, 1987

Related U.S. Application Data

[62] Division of Ser. No. 922,928, Oct. 24, 1986.

[51] Int. Cl.$^4$ ................................................ C07F 9/65
[52] U.S. Cl. ...................................... 548/113; 548/110; 260/502.5 G
[58] Field of Search ............................... 548/110, 113

[56] References Cited

FOREIGN PATENT DOCUMENTS 0018415 11/1980 European Pat. Off. .

OTHER PUBLICATIONS

Suzuki et al., Chemical Abstracts, vol. 93 (1980), 46824v.

Primary Examiner—Richard L. Raymond
Attorney, Agent, or Firm—Frank D. Shearin

[57] ABSTRACT

Phosphinylbutanoic acids, such as phosphinothricin, can be prepared by reacting racemic 4-halo-2-phthalimidobutyrates with a tricoordinate phosphorus compound represented by the formula:

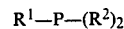

$$R^1-P-(R^2)_2$$

wherein $R^1$ is methyl or ethyl, and $R^2$ is selected from the group consisting of alkoxy having from one to six carbon atoms, aryloxy, and trialkylsilyloxy groups having from one to twelve carbon atoms, to form an intermediate compound; and hydrolyzing the intermediate compound to form the phosphinylbutanoic acids.

3 Claims, No Drawings

4-PHOSPHORUS-2-PHTHALIMIDOBUTYRATE INTERMEDIATES

This is a division of application Ser. No. 922,928, filed Oct. 24, 1986.

BACKGROUND OF THE INVENTION

This invention relates to a novel process for preparing the well known herbicide 2-amino-4-(hydroxymethylphosphinyl)butanoic acid, as well as other biologically active compounds, and to certain compounds useful as intermediates in the process.

The compound L-2-amino-4-(hydroxymethylphosphinyl)butanoic acid, also known in the art as phosphinothricin or glufosinate, is an effective broad spectrum phytotoxicant useful in controlling the growth of emerging seedlings and maturing and established woody and herbaceous vegetation. The compound can be represented by the formula:

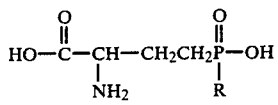

Phosphinothricin, where R is methyl, is a naturally occurring phosphinic acid analog of L-glutamate. Its activity has been attributed to an ability to inactivate the enzyme glutamine synthetase, thus blocking in vivo ammonia incorporation into amino acids and pyrimidines. Phosphinothricin was first isolated from two different streptomycete species, although the racemic P-ethyl analog was prepared considerably earlier and was shown to inhibit glutamine synthetase.

Rupp et al, U.S. Pat. No. 4,168,963, refer to earlier described methods for the preparation of phosphinothricin, which include base-catalyzed reactions of dialkyl acetamidomalonate esters with alkyl 2-haloethylmethylphosphinate esters or alkyl methylvinylphosphinate esters, as well as Strecker synthesis on 3-(alkoxymethylphosphinyl)propanoic aldehydes.

Minowa et al, U.S. Pat. No. 4,510,102, refer to other earlier described methods for the preparation of phosphinothricin, including the Michaelis-Arbuzov reaction of diethyl methylphosphonite with methyl 4-bromo-2-trifluoroacetamidobutanoate, a method characterized by low yields and instability of the brominated intermediate. Minowa et al further disclose a new preparation of phosphinothricin which involves the coupling of vinyl magnesium halides with alkyl methylphosphinyl halides, followed by base-catalyzed addition to the resulting alkyl methylvinylphosphinates of certain Schiff bases of alkyl glycinates, and subsequent hydrolysis.

Minowa et al, U.S. Pat. No. 4,499,027, disclose a new preparation of optically pure isomers of phosphinothricin which involves the base-catalyzed addition to alkyl methylvinylphosphinates of certain Schiff bases prepared from alkyl glycinates and optically active 2-hydroxypinan-3-ones.

Although these and other methods are available for the preparation of phosphinothricin, they are characterized by the use of strong bases and/or harsh conditions which are necessary to achieve the final end product. Thus, there still remains a need for processes to prepare phosphinothricin, its P-ethyl analog, and other phosphinylbutanoic acids, which produce the desired products in high yields and without the use of strong base or harsh conditions.

SUMMARY OF THE INVENTION

These and other advantages are achieved by a process for preparing phosphinylbutanoic acids by the steps of:

bringing together under reaction conditions a racemic 4-halo-2-phthalimidobutyrate represented by the formula:

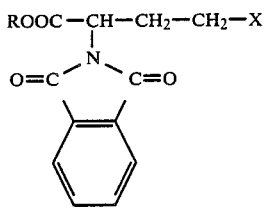

wherein R is selected from the group consisting of alkyl having one to about six carbon atoms and aryl, and X is selected from the group consisting of chlorine, bromine and iodine; and a phosphorus compound represented by the formula:

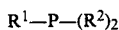

wherein $R^1$ is methyl or ethyl, and $R^2$ is selected from the group consisting of alkoxy having from one to six carbon atoms, aryloxy, and trialkylsilyloxy groups having from one to twelve carbon atoms, to form an intermediate compound; and hydrolyzing the intermediate compound to form the phosphinylbutanoic acids.

There is also provided a novel intermediate compound for such a process represented by the formula:

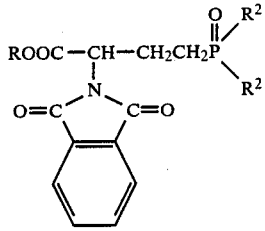

wherein R and $R^2$ are as described above.

DETAILED DESCRIPTION OF THE INVENTION

The 4-halo-2-phthalimidobutyrate, useful as a starting material in the process of the present invention, is known to the art. The compound can be prepared in two steps from crystalline 2-phthalimidobutyrolactone, which can be prepared by the reaction of potassium phthalimide with 2-bromobutyrolactone in a suitable solvent, such as dimethylformamide, at about 100° C. The 2-phthalimidobutyrolactone may contain some phthalimide, but it is useful in the next step; however, if desired, it can be purified in about a 75% yield by two recrystallizations from a water/acetone mixture.

The lactone can be dissolved in glacial acetic acid and anhydrous hydrohalide acid and allowed to stand for 24 hours to obtain the 4-halo-2-phthalimidobutanoic acid. The acid can be esterified by non-basic esterification procedures. The use of basic reaction conditions is to be avoided since the lactones have been found to re-form under such conditions. Suitable procedures include: esterification with diazoalkanes; treatment with an alcohol in the presence of a dialkylcarbodiimide; esterification with an alcohol solution containing an alkylsulfonic or mineral acid catalyst; and treatment with trialkyl orthoesters containing an acid catalyst.

As will occur to those skilled in the art, the ester moiety on the 4-halo-2-phthalimidobutyrate can vary within wide limits. The ester moiety can be selected from the group consisting of alkyl having from 1 to about 6 carbon atoms, for example, methyl, ethyl, isopropyl, or even a cyclic alkyl group, for example, cyclohexyl. The ester grouping also can be an alkyl group substituted with a benzyl or other inert group. The group can also be an aryl, for example, a phenyl group or a substituted phenyl group. Alkyl groups are preferred, and lower alkyl groups such as methyl or ethyl are especially preferred.

The halo-2-phthalimidobutyrate can then be brought together under reaction conditions with a trivalent phosphorus compound to form a racemic 4-phosphinylbutyrate. Generally, the reaction conditions involve heating the 4-halo-2-phthalimidobutyrate with between 1 and 2 molar equivalents of a trivalent phosphorus compound in an anhydrous non-hydrolytic and non-halogenated solvent, such as benzene, toluene, tetrahydrofuran, and the like. Temperatures can range between about room temperature and about 125° C., but at room temperatures the reaction is quite sluggish, and excessively high temperatures will cause decomposition. Temperatures at the boiling point of the solvent or at a lower temperature, such temperatures usually being below about 125° C., are satisfactory. Moisture should be excluded from the reaction conditions, and in the case of oxidatively unstable trivalent phosphorus compounds, oxygen should be excluded.

The trivalent phosphorus compound can be represented by the formula

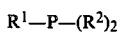

wherein $R^1$ is methyl or ethyl and each $R^2$ is selected from the group consisting of alkoxy having 1 to about 6 carbon atoms, aryloxy, and trialkylsilyloxy groups having from one to twelve carbon atoms. Suitable alkoxy groups include methoxy, ethoxy, isopropyloxy, butoxy, and the like, as well as cyclic alkyloxy groups, such as cyclohexyloxy. The alkoxy group can also be substituted, with say a phenyl group. The aryloxy group can be a phenoxy group, or a phenoxy group substituted with an alkyl and the like. Suitable trialkylsilyloxy groups include trimethylsilyloxy, triethylsilyloxy, ethyldimethylsilyloxy, and the like, wherein the total number of carbon atoms in the group can vary from three to twelve or higher, although there is no advantage to the use of trialkylsilyloxy groups having more than about twelve carbon atoms. It is preferred to use alkoxy groups, and methoxy, ethoxy, isopropyloxy and butoxy are especially preferred.

From these reaction conditions, there is then formed an intermediate compound represented by the structure:

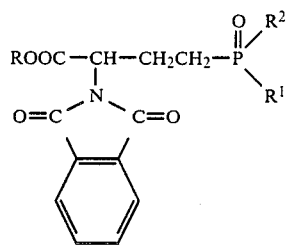

wherein R, $R^1$ and $R^2$ are as defined above.

In the process of the present invention, the intermediate compound described above is then hydrolyzed to the desired phosphinothricin, its P-ethyl analog, or other phosphinylbutanoic acids, depending on the values of R. Hydrolysis can mean any procedure known to those skilled in the art which is designed to cleave hydrolytically, either simultaneously or in a stepwise fashion, all of the ester and amide groups found in the intermediate compound to provide the desired end product. Suitable hydrolysis procedures include, but are not limited to: heating with a concentrated aqueous solution of a strong mineral acid, such as hydrochloric acid, sulfonic acid, and the like; saponification with an aqueous alkali metal hydroxide solution, such as sodium hydroxide, potassium hydroxide, and the like, followed by acid hydrolysis; hydrazinolysis, or similar amine mediated cleavage of a phthaloyl group, followed by acid hydrolysis; cleavage of the phthaloyl group with an alkali borohydride salt in an alcoholic medium, followed by acid hydrolysis; cleavage of phosphinate esters with trialkylsilyl halides, followed by carboxylate ester and phthaloyl group hydrolysis. However, because of the simplicity of the procedure and the elimination of unwanted byproducts, heating with a concentrated aqueous solution of a strong mineral acid, such as hydrochloric acid or sulfuric acid, is preferred, and the use of hydrochloric acid is especially preferred. The temperature of the acid hydrolysis can be determined by routine experimentation by those skilled in the art, but it is preferred to use temperatures above about 75° C.

In another embodiment of this invention, the 4-halo-2-phthalimidobutyrate is brought together with a tricoordinate phosphorus compound represented by the formula

where $R^2$ selected from the group consisting of alkoxy having from one to six carbon atoms, aryloxy, and trialkylsilyloxy groups having from one to twelve carbon atoms to form a novel intermediate compound represented by the formula

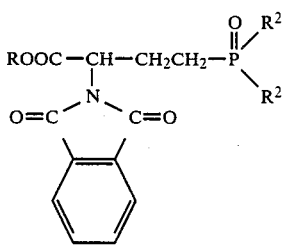

where R and R² are as defined above. Preferably R² is alkoxy, and methoxy and ethoxy are especially preferred.

This novel intermediate is useful in the preparation of racemic 2-amino-4-phosphonobutyric acid (DL-APBA), a known antagonist of glutamatergic neurotransmission, and other useful amino acids.

The invention is further illustrated by, but not limited to, the following examples. In all of the examples, 1H NMR spectra were recorded on a continuous-wave spectrometer at 60 MHz; shifts are reported as ppm downfield from tetramethylsilane. 31P NMR spectra were recorded at 40 MHz on a fourier-transform spectrometer using proton irradiation and external deuterium lock; shifts are reported as ppm downfield from 85% $H_3PO_4$.

EXAMPLE 1

DL-4-BROMO-2-(1,3-DIHYDRO-1,3-DIOXO-2H-ISOINDOL-2-YL)BUTANOIC ACID

A lactone was prepared by the reaction of a slight excess of 2-bromo-4-butyrolactone with potassium phthalimide in dimethylformamide at 100° C. The lactone (115.5 g, 0.5 mole) was suspended in 1500 ml glacial acetic acid, and a steady stream of anhydrous hydrobromic acid was passed through the mechanically stirred mixture until the starting material dissolved (about 1 hour), and for 1 hour thereafter. After standing for 12 hours, the solution was evaporated, in vacuo, and the residue was dissolved in diethyl ether, which was boiled with neutral charcoal, filtered, and diluted with hexane. The product (148 g, 95%) was obtained after crystallization as large prisms, m.p. 121°–123° C.

1H NMR (CDCl3): 2.75 (2H, q, J=3.5), 3.45 (2H, m), 5.20 (1H, t, J=4), 7.80 (4H, m).

Analysis ($C_{12}H_{10}BrNO_4$): Calculated, C 46.18, H 3.23, N 4.49; Found, C 46.24, H 3.26, N 4.49.

EXAMPLE 2

METHYL DL-4-BROMO-2-(1,3-DIHYDRO-1,3-DIOXO-2H-ISOINDOL-2-YL)BUTANOATE

An ethereal solution of the product from Example 1 (30 g, 96 mmol) was cooled to 0° C. and treated with excess ethereal diazomethane until a yellow color persisted which was discharged upon dropwise addition of glacial acetic acid. Dilution with hexane and crystallization afforded the product (29.7 g, 95%) as large prisms, m.p. 41°–43° C. 1H NMR (CDCl3): 2.77 (2H, q, J=3.5), 3.37 (2H, m), 3.70 (3H, s), 5.12 (1H, t, J=3.5), 7.78 (4H, m).

Analysis ($C_{13}H_{12}BrNO_4$): Calculated: C, 47.87; H, 3.71; N, 4.29; Found, C, 47.98; H, 3.72; N, 4.28.

EXAMPLE 3

METHYL DL-4-BROMO-2-(1,3-DIHYDRO-1,3-DIOXO-2H-ISOINDOL-2-YL)BUTANOATE

A solution of the product from Example 1, X=Br, (200 g, 0.64 mole) in 1.0 liter of 3/2 2,2-dimethoxypropane/methanol containing 50 ml of concentrated hydrochloric acid was allowed to stand for 64 hours, whereupon solvents were evaporated in vacuo. The residue was partitioned between ether and saturated aqueous sodium bicarbonate, and the organic phase was washed with brine, dried with magnesium sulfate, filtered and evaporated in vacuo to give the crude product (229 g) as a yellow oil. This material was treated with silica gel in ether to remove polar impurities, and the ethereal filtrate was boiled with neutral charcoal, filtered and diluted with hexane. The pure product (153 g, 73%) was obtained after crystallization as described in Example 2. Additional material of sufficient purity for further reactions could be obtained by further crystallizations from the initial mother liquor.

EXAMPLE 4

METHYL DL-2-(1,3-DIHYDRO-1,3-DIOXO-2H-ISOINDOL-3-YL)-4-IODOBUTANOATE

A solution of the product of Example 3 (6.52 g, 20 mmol) and sodium iodide (7.49 g, 50 mmol) in 250 ml of dry acetone was heated at reflux for 12 hours. After evaporation of solvent in vacuo, the residue was partitioned between ether and saturated aqueous sodium bisulfite. The organic phase was washed with brine, dried with magnesium sulfate, filtered and partially evaporated in vacuo. Dilution with hexane and crystallization afforded the product (7.24 g, 97%) as large prisms, m.p. 57°–59° C. 1H NMR (CDCl3): 2.85 (2H, m), 3.25 (2H, m), 3.74 (3H, m), 5.08 (1H, t, J=3.5), 7.82 (4H, m).

Analysis ($C_{13}H_{12}INO_4$): Calculated, C, 41.85; H, 3.24; N, 3.75; Found, C, 41.91; H, 3.36; N, 3.81.

EXAMPLE 5

METHYL DL-2-(1,3-DIHYDRO-1,3-DIOXO-2H-ISOINDOL-2-YL)-4-(ETHOXYMETHYLPHOSPHINYL)-BUTANOATE

A solution of the product from Example 3 (6.52 g, 20 mmol) and diethyl methylphosphonite (5.44 g, 40 mmol) in 30 ml of dry toluene was heated at reflux in an atmosphere of dry nitrogen for 16 hours, the progress of the reaction being monitored by periodic sampling for 1H and 31P NMR. The toluene was evaporated in vacuo, and the residue was heated at 80° C. and 1 mm Hg to remove volatile phosphinates. Chromatography of the crude product on silica gel using 4/1 ethyl acetate isopropanol showed unchanged starting material (1.90 g), and pure product (4.87 g, 97% based on recovered starting material) as a colorless syrup. 1H NMR (CDCl3): 1.30 (3H, t, J=3), 1.50 (3H, d, J=7), 1.65–2.80 (4H, m), 3.75 (3H, s), 4.10 (2H, quin, J=3), 4.95 (1H, t, J=3.5), 7.92, (4H, m). 31P NMR (CDCl3): 54.25.

Analysis ($C_{16}H_{20}NO_6P+1.2H_2O$): Calculated, C 51.26, H 6.02, N 3.74; Found, C 51.25, H 5.73, N 3.60.

The structure of the compound can be represented as:

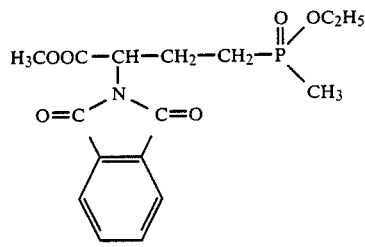

EXAMPLE 6

DL-2-AMINO-4-(HYDROXYMETHYLPHOSPHINYL)BUTANOIC ACID (DL-PHOSPHINOTHRICIN)

A solution of the product of Example 5 (4.30 g, 12.2 mmol) in 60 ml of 6N hydrochloric acid containing 5 ml of glacial acetic acid was heated at reflux for 24 hours. Evaporation of solvents in vacuo, followed by trituration with cold water and removal of precipitated phthalic acid, afforded the crude hydrochloride salt as a foam after evaporation of water. This material was dissolved in 10 ml of methanol at 0° C., propylene oxide (1.43 g, 24 mmol) was added, and the solution was allowed to stand 12 hours at 0° C. Filtration of the precipitated product, followed by azeotroping with water and evacuation, afforded pure DL-phosphinothricin (1.90 g, 86%) as a white foam. 1H NMR (D20): 1.46 (3H, d, J=7), 1.55–2.45 (4H, m), 4.00 (1H, t, J=3). 31P NMR (D20): 50.07.

Analysis ($C_5H_{12}NO_4P + 0.7H_2O$): Calculated, C 31.00, H 6.97, N 7.23; Found, C 30.81, H 6.71, N 7.05.

EXAMPLE 7

METHYL DL-4-(DIETHOXYPHOSPHINYL)-2-(1,3-DIHYDRO-1,3-DIOXO-2H-ISOINDOL-2-YL)BUTANOATE

A solution of the product of Example 3 (5.0 g, 15.3 mmol) in 50 ml of triethyl phosphite protected from moisture was heated at 125° C. for 16 hours. Solvent and volatile phosphonates were removed by heating at 80° C. and 1 Torr, and chromatography of the residue on silica gel using ethyl acetate afforded the purified phosphonate (5.50 g, 94%) as a colorless oil. 1H NMR (CDCl3): 1.30 (6H, t, J=3), 1.35–2.87 (4H, m), 3.72 (3H, s), 4.08 (4H, quin, J=3), 4.87 (1H, t, J=3), 7.80 (4H, m). 31P NMR (CDCl3): 30.08.

Analysis ($C_{17}H_{22}NO_7P + 0.6H_2O$): Calculated, C, 51.80; H, 5.93; N, 3.55; Found C, 51.78; H, 5.67; N, 3.56.

EXAMPLE 8

METHYL DL-2-(1,3-DIHYDRO-1,3-DIOXO-2H-ISOINDOL-2-YL)-4-(DIMETHOXYPHOSPHINYL)BUTANOATE

Reaction of the product from Example 3 with trimethyl phosphite in the manner described for Example 7 afforded the phosphonate as small prisms, recrystallized from ether-ethyl acetate, m.p. 93°–95° C. 1H NMR (CDCl3): 1.45–2.85 (4H, m), 3.64 (6H, d, J=5), 3.66 (3H, s), 4.82 (1H, t, J=3), 7.69 (4H, m). 31P NMR (CDCl3): 32.68.

Analysis ($C_{15}H_{18}NO_7P$): Calculated, C, 50.71; H, 5.11; N, 3.94; Found, C, 50.71; H, 5.14; N, 3.88.

EXAMPLE 9

DL-2-AMINO-4-(DIHYDROXYPHOSPHINYL)BUTANOIC ACID (DL-2-AMINO-4-PHOSPHONOBUTYRIC ACID, DL-APBA)

A solution of the phosphonate product from Example 7 (1.75 g, 4.6 mmol) in 50 ml of concentrated hydrochloric acid containing 5 ml of glacial acetic acid was heated at reflux for 24 hours. Evaporation of solvents in vacuo, followed by trituration with cold water and removal of precipitated phthalic acid, afforded the crude hydrochloride salt as a foam after evaporation of water. This material was dissolved in 15 ml of methanol at 0° C., propylene oxide (0.44 g, 7.7 mmol) was added, and the solution was allowed to stand 12 hours at 0° C. Filtration of the precipitated product, followed by azeotroping with water and crystallization, afforded pure DL-APBA (0.70 g, 84%) as colorless prisms, m.p. 210°–213° C. 1H NMR (D20): 2.05 (4H, m), 4.09 (1H, m). 31P NMR (D20): 24.47.

Analysis ($C_4H_{10}NO_5P + 1.0H_2O$): Calculated, C, 23.89; H, 6.01; N, 6.96; Found, C, 23.85; H, 6.02; N, 6.94.

EXAMPLE 10

METHYL 1-(1,3-DIHYDRO-1,3-DIOXO-2H-ISOINDOL-2-YL)CYCLOPROPANOATE

A solution of the product from Example 3 (R=CH3, X=Br, 15.0 g, 46.0 mmol) in 30 ml of dry tetrahydrofuran was added dropwise to a suspension of hexane-washed sodium hydride (50% oil dispersion, 2.65 g, 55.2 mmol) in 60 ml of dry tetrahydrofuran. The resulting mixture was stirred for 12 hours and partitioned between ether and brine, and the organic phase was washed with brine, dried with magnesium sulfate, filtered and evaporated in vacuo to give the crude product (10.5 g) as a white solid. Recrystallization from ether-hexane afforded the purified ester (10.2 g, 86%) as small prisms, m.p. 139°–141° C.

1H NMR (CDCl3): 1.60 (4H, two dd, J=9/3, 15/5), 3.60 (3H, s), 7.65 4H, m).

Analysis ($C_{13}H_{11}NO_4$): Calculated, C, 63.67; H, 4.52; N, 5.71; Found, C, 63.68; H, 4.56; N, 5.67.

EXAMPLE 11

1-AMINOCYCLOPROPANECARBOXYLIC ACID (ACC)

A solution of the ester from Example 10 (10.0 g, 40.8 mmol) in 200 ml of 6N HCl was heated at reflux for 12 hours. Evaporation of solvent in vacuo, followed by trituration with cold water and removal of precipitated phthalic acid, gave the crude product as a white solid. Recrystallization from water-acetone afforded ACC hydrochloride (5.30 g, 95%) as small needles, m.p. 220°–222° C. 1H NMR (D20): 1.40 (m).

Analysis ($C_4H_8ClNO_2$): Calculated, C, 34.47; H, 5.93; N, 10.05; Cl, 25.44; Found, C, 34.39; H, 5.93; N, 10.10; Cl, 25.27.

A solution of ACC hydrochloride (2.75 g, 20 mmol) in 100 ml of water containing 30 g of slightly basic Dowex WGR-2 resin was stirred for 3 hours. Filtration and evaporation of solvent in vacuo furnished crude ACC as a white solid. Recrystallization from water-ethanol furnished purified ACC as small plates, m.p. 231°–233° C. 1H NMR (D20): 1.25 (m).

Analysis ($C_4H_7NO_2$): Calculated, C, 45.11; H, 7.19; N, 13.15; Found, C, 44.80; H, 7.13; N, 13.03.

Although the invention has been described in terms of specified embodiments which are set forth in particular detail, it should be understood that this is by way of illustration only, and that alternative embodiments and operating techniques will become apparent to those skilled in the art in view of the disclosure. For example, the phthaloyl group of the intermediate compounds may be substituted with alkyl, aryl, or halogen substituents, or may be replaced by similarly substituted alkanedioyl or fused bicyclic or polycyclic aromatic groups, such as naphthalenedioyl and the like. Accordingly, modifications can be made without departing from the spirit of the described invention.

I claim:

1. A compound represented by the formula:

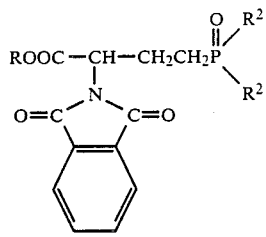

wherein R is selected from the group consisting of alkyl having one to six carbon atoms and aryl, and $R^2$ is selected from the group consisting of alkoxy having from one to six carbon atoms, aryloxy, and trialkylsilyloxy groups having from one to twelve carbon atoms.

2. A compound of claim 1 wherein $R^2$ is alkoxy.

3. A compound of claim 2 wherein $R^2$ is selected from the group consisting of methoxy and ethoxy.

* * * * *